United States Patent [19]

Grady et al.

[11] Patent Number: 4,541,108
[45] Date of Patent: Sep. 10, 1985

[54] X-RAY APPARATUS WITH TILTING TABLE

[75] Inventors: John K. Grady, Harvard; Paul G. Rice, Lincoln, Mass.

[73] Assignee: John K. Grady, Littleton, Mass.

[21] Appl. No.: 575,203

[22] Filed: Jan. 30, 1984

[51] Int. Cl.³ .................... G03B 41/16; G01N 21/00; G01N 23/00; G03D 11/00

[52] U.S. Cl. ........................................ 378/196; 378/20; 378/177; 378/179; 378/209; 378/189

[58] Field of Search ............... 378/177, 179, 189, 196, 378/209, 20

[56] References Cited

U.S. PATENT DOCUMENTS

| | | | |
|---|---|---|---|
| 3,281,598 | 10/1966 | Hollstein | 378/179 |
| 3,670,163 | 6/1972 | Lajus | 378/179 |
| 3,708,662 | 1/1973 | Kurokawa et al. | 378/179 |
| 4,481,656 | 11/1984 | Janssen et al. | 378/196 |

Primary Examiner—Richard L. Schilling
Attorney, Agent, or Firm—James H. Grover

[57] ABSTRACT

X-ray apparatus has a rotor on a standard, the rotor including two rings, one fixed on the rotor and the other rotating on an axis normal to the rotor axis. Posts on the rotating ring parallel to its axis carry an X-ray tube and an X-ray receptor on a radiation axis intersecting the ring axis at an isocenter and capable of angulation about the isocenter. A patient table is slidingly mounted on the fixed rotor ring extending through apertures in both rings. Turning of the rotor tilts the patient table in a head to foot direction while turning of the rotating ring revolves the patient on his own axis.

11 Claims, 3 Drawing Figures

X-RAY APPARATUS WITH TILTING TABLE

BACKGROUND OF THE INVENTION

In one form of conventional X-ray apparatus an X-ray tube and a receptor, such as film or a scintillation screen, are mounted on one frame, and a human patient or like subject lies on a table which is wheeled into a radiation axis between the tube and receptor for examination by an X-ray beam on the radiation axis. If the table and receptor are on a moveable frame, the angle of the radiation axis through the patient may be adjusted for the best exposure of a particular patient organ. But the table may not be tilted to place the patient in a position other than a horizontal position, and there are many X-ray examining procedures in which a horizontal position is not desirable. Heart and kidney examinations are usually best conducted with the patient in a natural position such as standing erect or inclined as when leaning. Some patients do not breathe easily prone, and examination must be interrupted periodically to raise their heads. In other cases a physician's access to a particular area of a patient is greatly improved by inclining the patient. Patients undergoing gastro-intestinal examination may be placed on an inclining table having an X-radiation source and fluoroscopic screen fixed on it as the table and patient are raised to upright position, but examination is limited to exposures at a fixed angle through the gastro-intestinal area of the patient.

Accordingly it is one object of the present invention to provide X-ray apparatus in which not only may the patient table be inclined to an erect or leaning position, but also the radiation axis may be angulated and fixed angularly relative to the patient in any of the table positions.

Other objects of the invention are to allow longitudinal movement of the patient table along its axis and bidimensional movement of the table in a plane normal to its longitudinal axis.

SUMMARY OF THE INVENTION

According to the invention X-ray apparatus comprises a standard; a horizontal rotor journalled in the standard to turn about the rotor axis; an elongate patient table mounted on the rotor with the longitudinal table axis directed transversely of the rotor axis; and a radiation set including an X-ray source and an X-ray receptor on a radiation axis intersecting the table axis, and rotating means on the rotor to support the set for angulation of the radiation axis around the table, whereby the head of a patient may be elevated or lowered relative to the patient's body while changing the angular relation of the radiation axis to the patient.

Further according to the invention the rotor has an aperture therethrough transverse its axis of rotation and the patient table is slidingly mounted on the rotor for longitudinal adjustment of the patient. Preferably the rotor has an aperture there through and includes first means for adjusting the table in a first direction radially of the table axis.

DRAWINGS

DESCRIPTION

Figure 1:
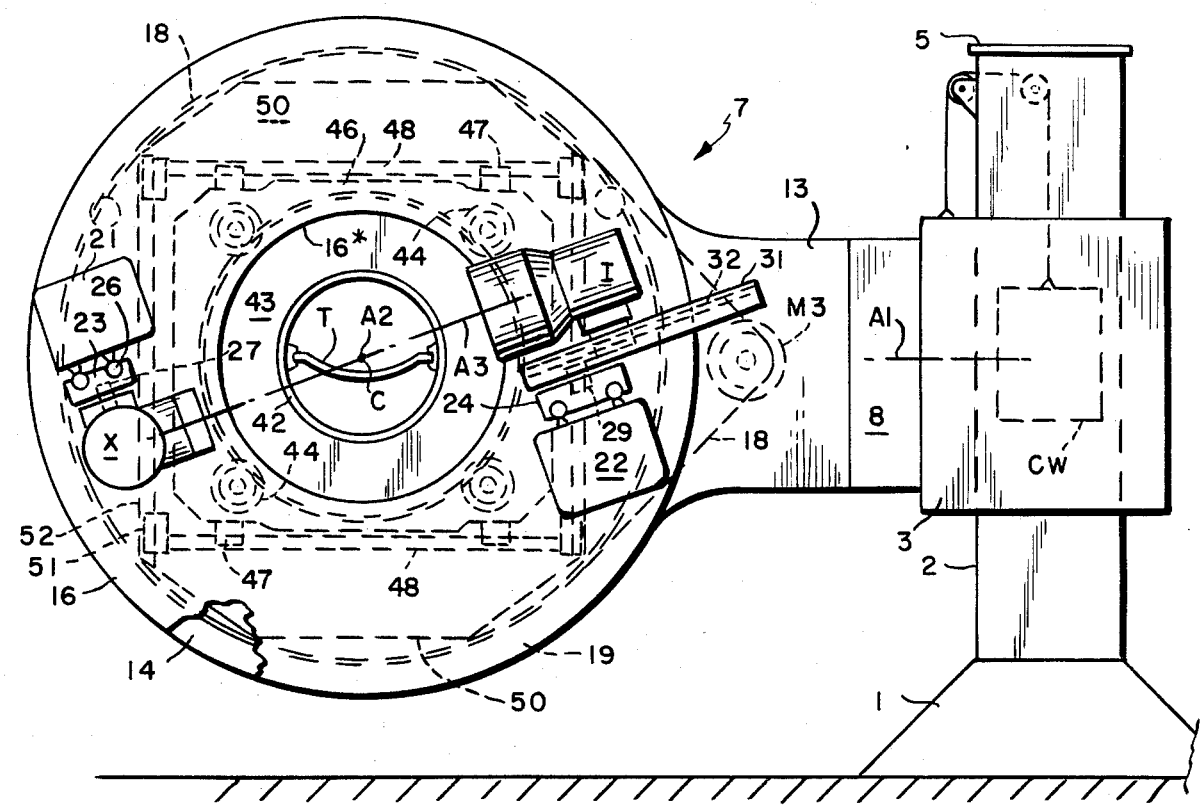
FIG. 1 is a side elevation of X-ray apparatus according to the invention.
Figure 2:
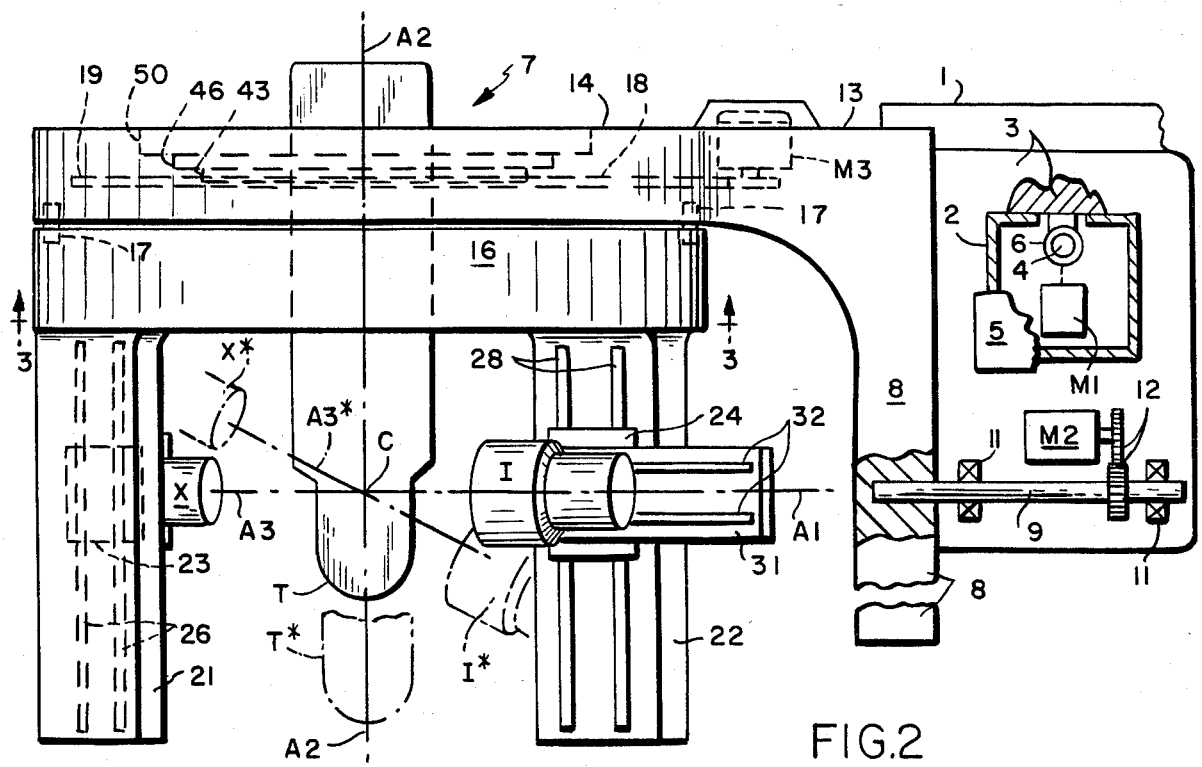
FIG. 2 is a plan view of the apparatus.

The X-ray apparatus shown in FIGS. 1 and 2 has a base 1 anchored on the floor of an examination room. A hollow rectangular column 2 having a cap 5 forms with the base 1 a standard on which a collar 3 reciprocates vertically counterbalanced by a weight CW driven by a first motor M1 within the column which turns a vertical screw 4 carrying a nut 6 attached to the collar. Extending horizontally from the collar 3 is a rotor assembly 7 including an arm 8 fixed to a shaft 9 rotating in bearings 11 on the collar. The arm 8 is of sufficient length and mass to counterweight the remainder of the rotor assembly. The shaft 9 and rotor 7 are turned on an axis A1 by a second motor M2 through gearing 12.

Extending from the rotor arm 8 is a short beam 13 integrally connected to a first, rear ring 14 of the rotor. A second, front ring 16 is connected to the rear ring by a circular bearing 17 for rotation about an axis A2 through the rings. The front ring 16 is driven by a motor M3 on the rear ring by a belt or sprocket chain 18 around a sheave 19 extending from the front ring 16 inside the rear ring.

Extending from the front ring 16 parallel to its axis A2 and diametrically opposed are two rectangular posts 21 and 22 respectively carrying carriages 23 and 24 for an X-ray tube X and an X-ray receptor, e.g. an image intensifier I. As is well known in the art, the tube X radiates a beam of X-rays along a radiation axis A3 to the receptor I which converts the X-rays to a light image for still or cine photography, or to electrical signals for data processing and display. The X-ray carriage 23 slides on rods 26 mounted on the post 21 for reciprocation parallel to the rotational axis A2 of the first ring 16, and the tube is further connected to the carriage by a rotary bearing 27 also to allow rotation of the tube as illustrated by the tube position X* of FIG. 2. The receptor carriage 24 similarly slides on rods 28 on the post 22 for reciprocation parallel to the axis A2 and is connected by a rotary bearing 29 to a secondary carriage 31 having rods 32 on which the receptor I reciprocates along the radiation axis A3 to vary the image magnification of the receptor. The X-ray tube X thus has a linear movement and a rotary movement; the receptor I having two linear movements at right angles and a rotary movement. These movements are customarily motor driven and the rotary movements around bearings 27 and 29, and the linear movements along the posts 21 and 22 of the front ring parallel to its rotational axis A2 are coordinated electrically so that as the tube and receptor reciprocate in opposite directions from the solid line positions X and I of FIG. 2 to adjusted positions such as the phantom positions X* and I* they are appropriately inclined to maintain their radiation axis A3* intersecting the rotational axes A1 and A2 at a fixed isocenter C. During examination the isocenter is preferably at an internal organ or other zone of the patient.

Adjacent the isocenter C an elongate table T for a patient P extending through apertures 14* and 16* respectively through the rear and front rings 14 and 16 transverse the rotor axis A1 is slidingly supported by linear bearings 41 of a multiple frame assembly anchored on the rear ring 14 around the openings 14* and 16*. As shown in detail in FIG. 3 the linear bearings 41 are attached to the flange 42 of an inner ring 43 rotationally supported on four rolls 44 journalled on a first, horizontally adjustable subframe 46. The first subframe 46 has at its top and bottom horizontal linear bearings 47 sliding on bearing rods 48 secured to a second subframe 50 with an octagonal outline as shown. These bearings allow horizontal adjustment of the table at right angles to the axis A2 of the rear and front rings 14 and 16, and radially of the table axis.

The second subframe 50 in turn has linear bearings 51 reciprocating vertically of bearing rods 52 anchored on the rear wall 15 of the rear rotor ring 14 within the circumference of the sheave 19 extending from the front ring 16 into the rear ring. Two screws 56 held in thrust bearing blocks 57 on the rear wall 15 of the rear ring 14 vertically reciprocate nuts 58 anchored on the second subframe 50. Rotation of the screws 56 by a vertical adjust motor M4 raises or lowers the second subframe 50. Similarly the first subframe may be reciprocated horizontally by a motor drive.

The apparatus described presents a novel combination of patient and X-ray axis movements particularly well suited for angiographic examination over relatively short lengths of a patient, but at any short length from the head to foot of the patient and from many radiation angles from sphirical angles around the patient, and, most importantly, while inclining the patient relative to the horizontal at the optimum angle for the patient's condition and the appropriate examination procedure. For the patient may be tilted by elevation or lowering of his head by turning of the rotor 7 about its axis A1 and the patient may be rolled about his own axis by rotation of the table T on the ring axis A2. The patient may be moved longitudinally to bring any area of his body from head to foot within the range of the X-ray tube X and receptor I, within which range successive X-ray exposures may be made along a desired range of his body by reciprocation of the tube X and receptor I along the posts 21 and 22. In addition to these adjustments the X-ray tube X and receptor I may be rotated on the front ring 16 360° around the patient and through a limited angle, e.g. 90°, fore and aft of the patient. Such angular adjustments permit exposures from a substantial portion of the sphere around the patient at the isocenter. Also raising or lowering of the rotor 7 on the standard facilitates a physician's access to the patient during examination. And fine vertical and horizontal adjustments of the patient may be made relative to the rotor axis for clearer images of an organ or zone. Movement of the X-ray tube and receptor on the posts parallel to the table reciprocation allows adjusting the center of gravity of the patient and table to approach, or coincide with, that of the rotor and to increase physician access to the patient. These longitudinal patient movements may be coordinated to maintain the isocenter of radiation and rotation at the desired locus within the patient. The ability to slide the table to the neutral position shown minimizes the room space needed during fore and aft tilting of the table, and maximizes the angular extent of tilting.

Figure 3:
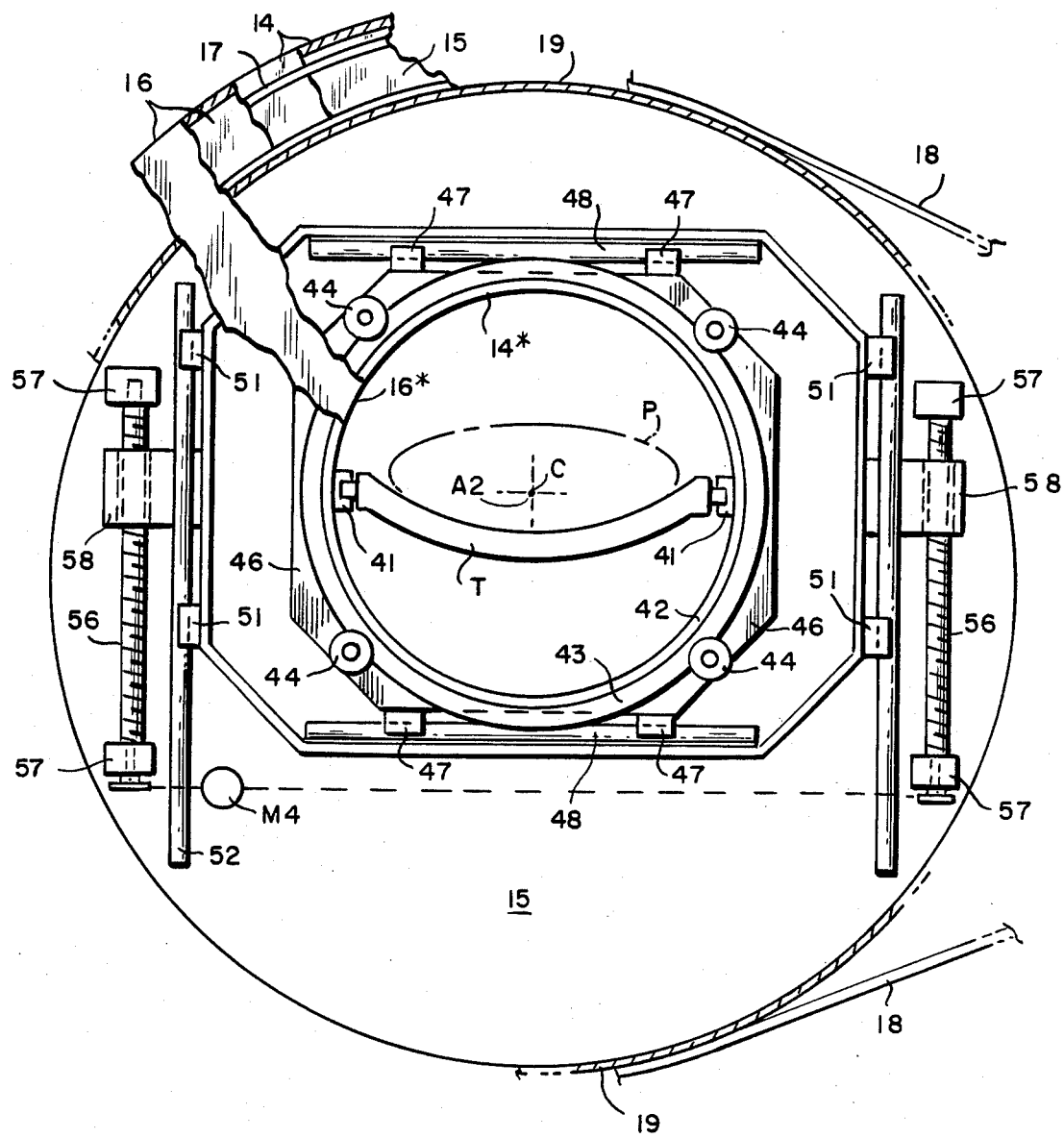
FIG. 3 is a partial side elevation like FIG. 1, enlarged and broken away to show internal portions of the apparatus.

It should be understood that reference to horizontal and vertical dispositions and movements of the apparatus are relative to the nominal showing of FIG. 3 and vary with adjusted positions of the apparatus as shown in FIGS. 1 and 2. Further it should be understood that the present disclosure is for the purpose of illustration only and that this invention includes all modifications and equivalents which fall within the scope of the appended claims.

We claim:

1. X-ray apparatus comprising:
   a standard;
   a horizontal rotor journalled in the standard to turn about the rotor axis;
   an elongate patient table mounted on the rotor with the longitudinal table axis directed transversely of the rotor axis; and
   a radiation set including an X-ray source and an X-ray receptor on a radiation axis intersecting the table axis, and rotating means on the rotor to support the set for angulation of the radiation axis around the table;
   whereby the head of a patient may be elevated or lowered relative to the patient's body while changing the angular relation of the radiation axis to the patient.

2. X-ray apparatus according to claim 1 including means reciprocating the rotor on the standard.

3. X-ray apparatus according to claim 1 wherein the rotor has an aperture there through transverse its axis of rotation and the patient table is slidingly mounted on the rotor for longitudinal adjustment of the patient.

4. X-ray apparatus according to claim 3 including table support means rotatively mounted on the rotor to rotate the table about an axis transverse of the rotor axis and extending through the aperture.

5. X-ray apparatus comprising:
   a standard;
   a horizontal rotor journalled in the standard to turn about the rotor axis;
   an elongate patient table mounted on the rotor with the longitudinal table axis directed transversely of the rotor axis; and
   a radiation set including an X-ray source and an X-ray receptor on a radiation axis intersecting the table axis, wherein the rotor has an aperture there through transverse its axis of rotation and the patient table is slidingly mounted on the rotor for longitudinal adjustment of the patient.

6. X-ray apparatus comprising:
   a standard;
   a horizontal rotor journalled in the standard to turn about the rotor axis;
   an elongate patient table mounted on the rotor with the longitudinal table axis directed transversely of the rotor axis; and
   a radiation set including an X-ray source and an X-ray receptor on a radiation axis intersecting the table axis, wherein the rotor has an aperture there through and includes first means for adjusting the table in a first direction radially of the table axis.

7. X-ray apparatus according to claim 1 wherein the rotor has an aperture there through and includes first means for adjusting the table in a first direction radially of the table axis.

8. X-ray apparatus according to claim 7 including second means for adjusting the table in a second direction radially of the table axis and substantially at right angles to the first direction.

9. X-ray apparatus according to claim 1 wherein the radiation set support comprises means to adjust the source and receptor parallel to the rotor axis.

10. X-ray apparatus according to claim 9 wherein the radiation set support comprises means to adjust the radiation axis of the source and receptor angularly relative to the rotor axis.

11. X-ray apparatus for radiological examination from head to foot along the body of a human patient comprising:
- a vertical standard for anchoring in an examination room, the standard including
- a collar vertically slidable on the standard and first motor means for raising and lowering the collar;
- a rotor journalled in the standard collar for rotation about its axis and second motor means for driving the rotor;
- a first ring on the rotor around an aperture there through with linear bearings transverse its axis of rotation;
- an elongate, X-ray transparent patient table slidingly mounted in the bearings to reciprocate along its longitudinal axis through the aperture;
- a second ring rotatably attached to the first ring around the aperture so as to rotate around the longitudinal axis through the aperture; and
- a radiation set on the second ring including an X-ray source and an X-ray receptor at opposite ends of a radiation axis intersecting the rotor axis at an isocenter adjacent the patient table, the second ring having arms respectively supporting the X-ray source and receptor and including means to adjust the source and receptor parallel to the rotor axis and angularly relative to the rotor axis;
- whereby the patient table may be tilted head to foot with respect to the horizontal without changing the angular relation of the radiation axis to the longitudinal axis of patient, and the table may be rolled around its longitudinal axis to adjust the angular of the radiation axis transversely of the patient.

* * * * *